United States Patent [19]

Danos et al.

[11] Patent Number: 4,551,270

[45] Date of Patent: Nov. 5, 1985

[54] DNA FRAGMENTS CODING FOR POLYPEPTIDES CONTAINING AT LEAST ONE ANTIGENIC DETERMINANT OF THE PAPILLOMAVIRUS, PARTICULARLY OF THE HPV 1A TYPE AND CORRESPONDING POLYPEPTIDES

[75] Inventors: Olivier Danos, Paris; Michael Katinka, Saint Mande; Moshe Yaniv, Paris, all of France

[73] Assignee: Institut Pasteur, Paris, France

[21] Appl. No.: 558,188

[22] PCT Filed: Apr. 1, 1983

[86] PCT No.: PCT/FR83/00063

§ 371 Date: Dec. 5, 1983

§ 102(e) Date: Dec. 5, 1983

[87] PCT Pub. No.: WO83/03623

PCT Pub. Date: Oct. 27, 1983

[30] Foreign Application Priority Data

Apr. 5, 1982 [FR] France .................. 82 05887

[51] Int. Cl.[4] ............................................. C07C 103/52
[52] U.S. Cl. .............................................. 260/112.5 R
[58] Field of Search ................................ 260/112.5 R Primary Examiner—Delbert R. Phillips
Attorney, Agent, or Firm—Weiser & Stapler

[57] ABSTRACT

Peptides having the following sequences are disclosed:
Leu-Asp-Gln-Phe-Pro-Leu-Gly-Arg-Lys-Phe-Leu,
Leu-Asp-Gln-Phe-Pro-Leu-Gly-Arg-Arg-Phe-Leu,
Ala-Lys-Arg-Arg-Arg-Lys, and
Ala-Lys-Lys-Lys-Lys-Lys.

5 Claims, 7 Drawing Figures

FIG.1a.

```
                                              début L2 →  MetValThrPheAspAsnProAlaPhe
961    aagaccctcttttaggccctcaagattctatataggcgtctatatg
       acaggtgcaagtacaagaccctagttcgttgagcagccacagtcaATGGTCACTTTTGATAATCCAGCATT GluProGluAspGluValSerIleIlePheGlnArgAspLeuAspLeuAlaLeuAlaGlnThrProValProGluPheArg
1081   TGAGCCAGAGCTTGATGAGGTGTCTATTATCTTCCAAAGAGACTTAGATGCTCTTGCTCAGACACCAGTGCCTGAATTTAGA
       AspValTyrLeuSerLysProThrPheSerArgGlu
       GATGTAGTTTATCTGAGCAAGCCCACATTTTCGCGGGA ProGlyGlyArgLeuArgValSerArgLeuGlyLeuLysSerSerThrIleArgThrLeuGlyThrAlaIleGlyAlaArgThr
1201   ACCAGGGGACGGTTAAGGGTTAGCCGCCCTTGGCAAAAGTTCAACTATTCGTACACGCCTGGGCACACAGCAATTGGGCCAGAACC
       HisPhePheTyrAspLeuSerSerIleAlaProGlu
       CACTTTTTCTATGATTTAAGTTCTATTGCTCCAGA AspSerIleGluLeuLeuProLeuGlyLeuHisSerGlnThrThrValIleSerSerAsnLeuGlyAspThrAlaPheIleGln
1321   AGACTCAATTGAATTATTGCCTTAGGTGAGCATAGTCAAACACAGTCATTAGTTCCAACTTAGGTGACACAGCATTTATACAA
       GlyGluThrAlaGluAspAlaAspLeuGluValIleSer
       GGTGAGACAGCAGAGGATGACTTAGAAGTTATCTC LeuGluThrProGlnLeuTyrSerGluGluLeuLeuAspThrAsnGluSerValGlyGluAsnLeuGlnLeuThrIleThr
1441   TTTAGAAACACCACAATTATATTCAGAAGAAGAGCTTTTAGACACAAACGAAAGTGTGGGCGAAAATTTGCAACTTACTATTACT
       AsnSerGluGlyGluValSerPheIleLeuLeuAspLeuThr
       AACTCAGAGGGTGAGGTTTCTATACTAGATTTAAC GlnSerArgValArgProProPheGlyThrGluAspThrSerLeuHisValTyrTyrProAsnSerSerLysGlyThrProIle
1561   ACAAAGCAGAGTCAGGCCACCTTTTGGCACTGAAGATACTAGCTTGCATGTATATTACCCAAATTCTTCTAAAGGGACTCCAATA
       IleAsnProGluGluSerPheThrProLeuValIle
       ATTAATCCTGAAGAATCATTTACACCTTTGGTTAT IleAlaLeuAsnAsnSerThrGlyAspPheGluLeuHisProSerLeuArgArgLysArgArgLysArgAlaTyrVal     Fin L2
1681   TATAGCTCTTAACAACTCAACAGGGATTTTGAGTTACATCCTAGTCTTAGAAAGCGTCGTAAAAGAGCTTATGTATAA        ***
1801                                   début L1 →    MetTyrAsnValPheGlnMetAlaValTrpLeuProAlaGlnAsnLysPhe
                                                     ATGTATAATGTTTTTCAGATGGCTGTCTGGTTACCAGGCGCAGAATAAGT
```

FIG.1b.

```
      IleAlaLeuAsnAsnSerThrGlyAspPheGluLeuHisProSerLeuArgLysArgArgLysAlaArgArgAlaTyrVal Fin L2
      TATAGCTCTTAACAACTCAACAGGGGATTTTGAGTTACATCCTAGTCTTAGAAAGCGTCGTAAAAGAGCTTATGTATAA
1681
1801                début L1 →  MetTyrAsnValPheGlnMetAlaValTrpLeuProAlaGlnAsnLysPhe
                                 ATGTATAATGTTTTCAGATGGCGTCTGTTACCAGGCAGAATAAGT
      TyrLeuProGlnProIleThrArgIleLeuSerThrAspGluTyrValThrArgThrAsnLeuPheTyrHisAlaThrSer
      TCTATCTTCCTCCCCAGCCATCACTAGAATCCTGTCCACTGATGAATATGTAACCAGAACCAATCTCTTCTACCATGCAACATCT
      GluArgLeuLeuValGlyHisProLeuPheGlu
      GAACGTCTACTGTCGGACATCCTTTGTTTG
1921
      IleSerSerAsnGlnThrValThrIleProLysValSerProAsnAlaPheArgValArgPheAlaAspProAsn
      AGATCCCAGTAATCAAACTGTAACTATACCAAAAGTGTCACCAAATGCATTTAGAGTTTTTAGGTGCGTTTTGCTGATCCAAAT
      ArgPheAlaPheGlyAspLysAlaIlePheAsnPro
      AGATTTGCATTTGGGGATAAGGCAATTTTAATC
2041
      GluThrGluArgLeuValPheGlyLeuArgGlyLeuIleGlyArgGlyGlnProLeuGlyIleGlyIleThrGlyHisPro
      CAGAAACAGAAAGATTAGTTTGGGCCTAAGAGGGATAGAGATAGGTAGAGCCAGCCTTTAGGTATAGGAATAACGGGCCACCCT
      LeuLeuAsnLysLeuAspAspAlaGluAsnProThr
      CTTTTAAATAAGTTAGATGATGCAGAAAATCCAA
2161
      AsnTyrIleAsnThrHisAlaAsnGlyLeuAspSerArgArgGlnAsnThrAlaPheAspAlaLysGlnThrGlnMetPheLeuMetPheValGly
      CAAATTATATTAATACTCACAAATGGAGATTCTAGACAAAATACTGCTTTGATGCAAAACAGACACAAATGTTCCTCGTCGGC
      CysThrProAlaSerGlyGlyHisTrpThrSerSer
      TGTACTCCTGCTTCAGGTGAACACTGGACAAGTA
2281
      ArgCysProGlyGluGlnValLysGlyLeuGluValLysAspCysProArgValGlnMetIleGluSerValIleGluAspGlyAspMetMet
      GTCGTTGCCAGGGGAACAAGTGAAACTTGGGACTGCCCCAGGTGCAAATGATAGAGTCTGTCATAGAAGATGTGACATGATG
      AspIleGlyPheGlyAlaMetAspPheAlaAlaLeu
      GATATTGGTTTTGGGGCTATGGATTTTGCTCTT
2401
      GlnGlnAspLysSerAspValProLeuAspTyrIleArgMetAsnHisGluAla
      TACAGCAAGACAAGTCTGATGTCCTTTAGATGTAGTTCAAGCAACATGCAAATATCTGAATATCAGAATCAAGCATGAAGGC
      TyrGlyAsnSerMetPhePheAlaArgArgGlu
      TATGGCAACTCTATGTTTTTTTTTGCACGTCGCG
```

FIG. 1c.

```
2521  GlnMetTyrThrArgHisPhePheThrArgGlyGlySerValGlyAspLysGluAlaValProGlnSerLeuTyrLeuThrAla
      AGCAAATGTATACCAGGCACTTTTTACTCGCGGGGTTCGGTGGGTTCGGTGGGTGATAAGGAGGCAGTCCCACAAAGCCTGTATTTAACAGCA
      AspAlaGluProArgThrThrLeuAlaThrThrAsn
      GATGCTGAACCAAGAACAACTTTAGCAACAACAA

2641  TyrValGlyThrProSerGlySerMetValSerSerAspValGlnLeuPheAsnArgSerTyrTrpLeuGlnArgCysGlnGly
      ATTATGTAGGCACACCAAGTGCTCTATGGTTTCATCTGATGTCCAATTGTTTAATAGATCTTACTGGCTTCAGCGATGTCAAGGC
      GlnAsnAsnGlyIleCysTrpArgAsnGlnLeuPhe
      CAGAATAATGGCATTTGCTGGAGAAACCAGTTAT

2761  IleThrValGlyAspAsnThrArgGlyThrSerLeuSerIleSerMetLysAsnAsnAlaSerThrThrTyrSerAsnAlaAsn
      TTATTACAGTTGGAGATAATACCAGAGGAACAAGTTTATCTATCAGTATGAAAAACAATGCAAGTACTACATATTCCAATGCTAAT
      PheAsnAspPheLeuArgHisThrGluGluPheAsp
      TTTAATGATTTTCTAAGACATACTGAAGAATTTG

2881  LeuSerPheIleValGlnLeuCysLysValLeuThrProGluAsnLeuAlaTyrIleHisThrMetAspProAsnIleLeu
      ATCTTTCTTTTATAGTTCAGCTTTGTAAAGTAAAGTTAACTCCCGAAAATCTAGCCTACATTCATACAATGGACCCTAATATTTTA
      GluAspTrpGlnLeuSerValSerGlnProProThr
      GAGGATTGGCAACTATCTGTATCTCAACCACCTA

3001  AsnProLeuGluAspGlnPheLeuGlySerSerLeuAlaAlaLysCysProGluGlnAlaProProGluProGlnThr
      CCAATCCTCTAGAAGATCAATATAGGTTTTAGGGTCTTCCTTGGCAGCAAAATGTCCAGAACAGGCGCCTCCTGAGCCCCAGACT
      AspProTyrSerGlnTyrLysPheTrpGluValAsp
      GATCCTTATAGTCAATATAAATTCTGGGAAGTCG

3121  LeuThrGluArgMetSerGlnLeuAspPheProLeuGlyArgLysPheLeuTyrGlnSerGlyMetThrGlnArgThr
      ATCTCACAGAAAGAGATGTCCGAACAATTAGACCAATTTCCACTAGGAAGGAAATTTCTATATCAAAGTGGCATGACACAACGTACT
      AlaThrSerThrThrLysArgLysThrValArg
      GCTACTAGTTCCACCACAAAGCCAAAACAGTGC
                                    Fin L1
3241  ValSerThrSerAlaLysArgAlaArgLysAla***
      GTGTATCTACGTCAGGCCAAGGCGTAAGGCTTTAG
3361
```

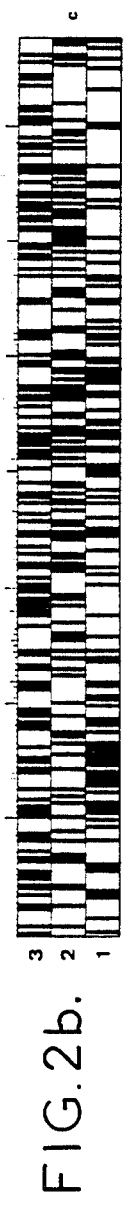
FIG. 2c.  FIG. 2a.  FIG. 2b.

FIG. 3.

```
                Thr  Glu  Arg  Met  Ser                Glu Gln  Leu Asp Gln Phe Pro Leu Gly Arg  Lys
HPV1a           A C   A G A A G  A T G  T C C          G A A C A A T T A G A C C A A T T C C A C T A G G A A G G A A A
                · ·   · · · · ·  · · ·  · · ·          · · · ·   · · · · · · · · · · · · · · · · · · · ·
BPV1            A A A G A A A A G C T T T C T          T T G G A C T T A G A T C A A T T T C C C T T G G G A A G A A G
                Lys  Glu  Lys  Leu  Ser                Leu Asp   Leu Asp Gln Phe Pro Leu Gly Arg  Arg

Phe Leu  Tyr  Gln              Ser Gly Met Thr                    Gln Arg  Thr Ala Thr  Ser Ser Thr
HPV1a           T T T C T A T   C A A           A G T G G C A T G A C A           C A A C G T A C T G C T A C T A G T T C C A C C
                · · · · · ·    · · ·           · · · · · · · · · · ·              · · · · ·  · · ·    · ·  · · · · · · · · ·
BPV1            T T T T A G C A G              G C A A G G G A T G T T C A        A C T G C T A C T G T G A G A A A C G A A G A
                Phe Leu  Ala Gln               Gln Gly Ala Gly Cys Ser             Thr  Ala Thr  Val Arg Lys Arg  Arg

Thr Lys  Arg                  Lys Thr Val Arg Val Ser Thr Ser   Thr Ala Lys  Arg Arg  Lys
HPV1a           A C A A A G C G               A A A A C A G T G C G T G T A T C T C C A G T C A G C C A A G C G G C G T A A G
                · · · ·  · · ·                · · · · · · · · · · · · · · · · · · · · · · · · · · · · ·
BPV1            A T T   A G C                 C A A A A A A C T T C C A A G C C T G C A A A A A A A A A A A A A A T A A A
                Ile  Ser                      Gln Lys  Ser Ser Lys Pro Ala Lys  Lys Lys Lys Lys

Ala
HPV1a           G C T T A G T A T A T A T T A T A T A A C T A T A T T T A T T A
                · ·   · · · · · · · · · · · · · · · · · · · · · · · ·   · · ·
BPV1            A G C T A A G T T T C T A A T G T T C T G T A A A T G T A A A A
```

DNA FRAGMENTS CODING FOR POLYPEPTIDES CONTAINING AT LEAST ONE ANTIGENIC DETERMINANT OF THE PAPILLOMAVIRUS, PARTICULARLY OF THE HPV 1A TYPE AND CORRESPONDING POLYPEPTIDES

The invention relates to DNA framents coding for polypeptides containing at least one antigenic determinant of the papillomavirus, particularly of the HPV 1a type. It also relates to transformation products of such polypeptides, such as those resulting from the conjugation through covalent linkages of these polypeptides to support macromolecules and having immunogenic properties enabling their use, particularly either as means of diagnosing the presence or not of a papillomavirus in biological specimens, or as active principle of vaccines capable of immunizing a host against these papillomaviruses.

It is known that papillomaviruses are capable of infecting a large number of living species, man being among these. They are responsible for the production of benign tumors, particularly verrucas at the level of the epithelium that they colonize. These tumors which have mostly a regressive character can nonetheless in a certain number of cases give rise to a malignant transformation. Besides, the papillomaviruses have from the morphological aspect, been considered as related to polyoma viruses, such as the viruses known under the names SV 40, BKV, etc. These various types of virus have in fact in common an icosahedric capsid structure containing a double DNA helix associated with histones. In spite of the recognized impossibility of cultivating these papillomaviruses on epithelial cells or other cells, in a tissue culture, O. Danos et al. have recently succeeded in cloning the whole genome of the human papillomavirus, of the type 1a, in an Escherichia coli strain (Eur. J. Biochem., 109, 457–461 (1980)).

The present invention results from the discovery of certain sequences of the genome of this papillomavirus, which are capable of coding for peptides or polypeptides which can contain antigenic determinants enabling their use as active principle of vaccines to be envisaged, as the case may be, after coupling with support macromolecules, at least for the smallest among them.

It is in this regard significant that these sequences are quite distinct from all sequences contained in the genomes of the polyoma viruses mentioned above. These sequences are revealed in fact to be borne by one only of the strands of the genome of the papillomavirus, as witnessed by sequence analyses of the whole genome of the papillomavirus.

The DNA fragment according to the invention can be redefined more generally, as consisting of that whose expression product in a suitable micro-organism contains at least one of the antigenic determinants of papillomaviruses, characterized in that it comprises a nucleotide sequence, itself contained or similar to that contained, either in the L1 region, or in the L2 region, or again for a part in the L1 region and for a part in the L2 region of that of the strands of the genome of a papillomavirus, such as the papillomavirus of the type 1a (HPV 1a) which comprises them and which are capable of coding for proteins of HPV 1a structures.

It is more particularly characterized in that it is constituted by a sequence of nucleotides capable of coding for one or some structure proteins of the virus or for a or some polypeptides having in common with these proteins a sequence containing at least one antigenic determinant characteristic of papillomaviruses, this nucleotide sequence being contained either in the L1 region, or in the L2 region, or again for a part in the L1 region and for a part in the L2 region, of that of the strands of the papillomavirus genome which includes them, said sequence being as the case may be completed by DNA fragments derived from the genome of the papillomavirus and normally associated in the latter with said genome, and including at the most a hundred nucleotides.

For convenience of description, reference will be made below to the drawings in which:

FIGS. 1a, 1b and 1c represent the structure of a part of one of the strands of the HPV 1a genome, more particularly of that of which the sequence is read from the 5' and to the corresponding 3' end;

FIGS. 2a and 2b are diagrammatic representations of the parts which, in the respective strands of the genome of HPV 1, are capable of being expressed in polypeptide form and FIG. 2c is a diagrammatic representation of the genome of a BPV 1 bovine papillomavirus;

FIG. 3 represents comparative structures of a preferred DNA fragment, according to the invention, derived from HPV 1a and of a corresponding fragment of the genome of bovine papillomavirus of type BPV 1.

FIGS. 1a, on the one hand, and 1b, 1c on the other hand, show the structures of the L1 and L2 regions of that of the strands of the genome of the HPV papillomavirus which carries it. These figures also show the aminoacyl residues coded by the successive triplets defined by the nucleotides of the strand concerned, these proteins corresponding to distinct reading phases of the corresponding nucleotide sequences. This is particularly what clearly appears in FIG. 1a, more particularly at the level of the number nucleotides 1870 to 1881, counting from the 5' end (not shown in FIG. 1). The relative positions of the L1 and L2 regions on the corresponding strand, in the direction of reading extending from the 5' end to the opposite end 3' of this same strand, result from examination of FIG. 2a, which shows the distributions of the region capable of giving rise to the expression, particularly when the corresponding DNA fragments, previously inserted in a vector, are used to transform suitable micro-organisms.

FIG. 2a corresponds to three possible reading phases of the corresponding strand, of which the 5' end would be situated at the left and the 3' end at the right of FIG. 2a. The codons are examined in groups of ten, each black stripe corresponding to those of said groups which, in the reading phase concerned, include a stop codon. The vertical stripes in dashed line correspond to the first ATG codon present in each of the sequences which follow and which are devoid of stop codons. The two EcoRI sites at the 4237 and 5240 positions aim at facilitating the diagrammatic orientation of the sequences resulting from the three possible reading phases, marked in the left of the figure by the numbers 3, 2 and 1. FIG. 2a takes into account the relative positions of the L1 and L2 regions which have been discussed above.

FIG. 2b takes into account reading possibilities under the same condition of the complementary strand of the DNA of the genome of HPV 1a. The presence is observed of a considerable number of stop codons extending over almost the whole of the corresponding strand, whatever the reading phase envisaged.

As has been indicated above, the invention relates among other things to DNA fragments capable of containing a zone common to the L1 region and to the L2 region, such a situation can occur on the occasion of the splice which can be produced between the two regions, at the time of transcription operations of these regions, within even transformed cells.

However, preferably, the invention relates to DNA fragments having common nucleotide sequences with the abovesaid L1 region of HPV 1a.

The more specific localization of those of the sequences contained in the L1 and L2 regions indicated above, which are capable of bearing an antigenic determinant characteristic of papillomaviruses, more particularly HPV 1a, can be operated in any case in known manner, particularly following the fragmentation of the corresponding DNA sequences, whether this is by suitable restriction enzymes of by chemical cleavage, by the integration of fragments obtained in a vector and the transformation of a suitable micro-organism by means of the vectors obtained and enabling the expression, by separation of the peptides obtained, the latter being then, as the case may be after coupling with a support macromolecule, used to induce the production of antibodies in a living host. There are then retained as fragments according to the invention those which are capable of producing antibodies able to neutralize HPV 1a in its entirety.

A preferred nucleotide sequence according to the invention consists of that which codes for the peptide sequence of formula:

Leu-Asp-Gln-Phe-Pro-Leu-Gly-Arg-Lys-Phe-Leu.

The peptide limited to this peptidic sequence is in particular coded by the nucleotide sequence:

TTA GAC CAA TTT CCA CTA GGA AGG
AAA TTT CTA.

This nucleotide sequence corresponds to those which extend from the positions 3148 to 3180 in FIG. 1*b*.

Another preferred fragment according to the invention contains a fragment coding for the following peptidic sequence:

Ala-Lys-Arg-Arg-Arg-Lys.

The peptide corresponding to this peptidic sequence is in particular coded by the nucleotide sequence:

GCC AAG CGC AGG CGT AAG.

The invention naturally relates also to all DNA fragments coding for structural proteins of other papillomaviruses, such as papillomavirus CRPV (abbreviation of "cottontail rabbit papillomavirus") and BPV1 (abbreviation of "bovine papillomavirus of type 1"). It is again also the same with peptides coded by these DNA fragment. Among these peptides figure particularly those corresponding to DNA sequences borne by the CPRV and BPV1 viruses mentioned above, these peptides being characterized by the following sequence:

CPRV:
Leu-Asp-Gln-Tyr-Pro-Leu-Gly-Arg-Lys-Phe-Leu.

BPV1:
Leu-Asp-Gln-Phe-Pro-Leu-Gly-Arg-Arg-Phe-Leu.

Also forming part of the invention are the DNA sequences of which the triplets are distinguished from those which have been stated above by a different nucleotidic structure, to the extent however that they code either for identical amino acids or again "equivalent" amino acids, it being understood that the expression "equivalent" aims here at denoting any amino acid which can be substituted for one of the amino acids of the basic structure without however essentially modifying the immunogenic properties of the corresponding peptides. In other words, equivalent amino acids will be those which permit the obtaining of a modified peptidic sequence, which, as the case may be after coupling with an adequate macromolecular support, permits the in vivo induction of antibodies which remain capable of neutralizing either the basic peptide, or again more generally the corresponding HPV 1a papillomavirus.

These equivalent aminoacyl groups can be determined either by relying on their structural homology, or on the results of crossed immunogenicity tests to which the different peptide sequences obtained are capable of giving rise.

By way of example, will be mentioned the possibilities of substitutions which can often be effected, without deep modification of the immunogenicity of the corresponding modified peptides, the replacement, for example, of leucine by valine or isoleucine, of aspartic acid by glutamic acid, of glutamine by asparagine, or arginine by lysine, etc., the reverse substitutions being naturally envisageable under the same conditions.

In this respect, it is interesting to point out the presence in the genome of bovine papillomavirus of BPV 1 type, of sequences showing a certain level of homology with corresponding sequences of HPV 1a, as results particularly from examination of FIG. 3.

FIG. 3 shows up in fact homologies which can be pointed out between the 3' end zone (extending from the nucleotide numbered 3246 from the 5' end of the genome of HPV 1a up to nucleotide 3476) of the L1 region along the corresponding reading code, and moreover a corresponding region of the genome of BPV 1. The latter region has been defined by sequential analysis of a recombinant obtained between the vector M13 described by ROTHSTEIN and WU (Gen. 15, 1981, 167–176) and/or MESSING J. et al (Nucl. Acids Res. (1981) 9, 309–321) and a fragment of BPV 1 bounded by ends Bgl II starting about 10 nucleotides before the end of the Hind III site of BPV 1 (diagrammatically shown in FIG. 2*c*). The dots placed between the letters opposite a nucleotidic sequence shown aims at stressing the identical character of the nucleotides concerned, the white spaces left free in each of the sequences having no other purpose than that of showing up still more distinctly the existing homologies. The common peptidic sequences coded by the corresponding sequences contained within the fragments concerned in FIG. 3 appear in the frames drawn.

Also forming part of the particular DNA fragments of the invention, are those which code for the peptides:

Leu-Asp-Gln-Phe-Pro-Leu-Gly-Arg-Arg-Phe-Leu and

Ala-Lys-Lys-Lys-Lys-Lys.

As particular nucleotidic fragments entering within the scope of the invention, will naturally be mentioned also those which are contained in the above-mentioned fragment of BPV 1, more particularly:

TTA GAT CAA TTT CCC TTG GGA AGA
AGA TTT TTA, GCA AAA AAA AAA AAA
AAA.

The invention relates naturally also to all equivalent DNA fragments, under conditions such as have been defined above.

The various DNA sequences such as have been described above, may be obtained, as has already been indicated, particularly by fragmentation of the genome and recovery of corresponding suitable fragments, containing the nucleotide chains corresponding to the sequences contained in the abovesaid regions L1 and L2 or again to smaller regions containing nonetheless specific antigenic determinants with regard to the whole virus. As regards the smallest fragments, particularly those which code for a limited number of amino acids, such as have been illustrated by the examples, it is also possible to resort to chemical synthesis of the corresponding nucleotides, according to methods well known today, the sequences obtained then being usable as inserts which can be incorporated in a vector permitting the transformation of microorganisms suited to their expression.

As regards the peptides themselves, it is possible also to resort, especially where peptides are concerned which only comprise a limited number of aminoacyl residues, to techniques known in themselves of chemical synthesis.

In this regard, recourse will be had to the method of synthesis in homogeneous solution described by Houben-Weyl in the work entitled "Methodem der Organischen Chemie" (Method of Organic Chemistry) edited by E. Wünsch., Vol. 15-I and II, THIEME, Stuttgart 1974.

This method of synthesis consists of condensing successively two by two the successive aminoacyls in the required order, or to condense aminoacyls and previously formed fragments and containing already several aminoacyl residues in the appropriate order, or again several fragments previously thus prepared, it being understood that care will be taken to protect beforehand any of the reactive functions borne by these aminoacyls or fragments with the exception of amine functions of the one and carboxyl functions of the other or vice versa, which must normally take part in the formation of peptidic linkages, particularly after activation of the carboxyl function, by methods well known in the synthesis of proteins. As a modification, recourse will be had to coupling reactions bringing into play conventional coupling reagents, of the carbodiimide type, such as, for example, 1-ethyl-3-(3-dimethylalinopropyl)-carbodiimide. When the aminoacyl employed possesses an additional amine function (the case of lysine, for example) or another acid function (case, for example, of glutamic acid), these functions will be, for example, protected, by carbobenzoxy or t-butyloxycarbonyl groups, as regards the amine functions or by t-butylester groups, as regards the carboxylic functions. It will be the same for the protection of any other reactive function. For example when one of the aminoacyls concerned contains an SH function (for example cysteine), recourse can be had to an acetamidomethyl or formamidomethyl groups.

In the case of progressive synthesis, amino acid by amino acid, the synthesis starts preferably by the condensation of the C-terminal amino acid with the amino acid which corresponds to the neighboring aminoacyl in the desired sequence and so on, step by step, up to N-terminal amino acid. According to another preferred technique of the invention, recourse is had to that described by R. D. Merrifield in the article entitled "Solid Phase Peptide Synthesis" (J. Am. Chem. Soc., 45, 2149-2154).

To manufacture a peptidic chain according to the Merrifield process, recourse is had to a very porous polymeric resin, on which the first C-terminal amino acid of the chain is fixed. This amino acid is fixed to the resin by means of its carboxylic group and its amine function is protected, for example by the t-butyloxycarbonyl group.

When the first C-terminal amino acid is thus fixed to the resin, the group protecting the amine function is removed by washing the resin with an acid.

In the case where the protective group of the amine function is the t-butyloxycarbonyl group, it can be removed by washing the resin by means of trifluoroacetic acid.

The second amino acid which provides a second aminoacyl of the desired sequence from the C-terminal aminoacyl residue is then made to react on the deprotected amine function of the first C-terminal amino acid fixed to the chain. Preferably, the carboxyl function of this second amino acid is activated, for example by dicyclohexylcarbodiimide, and the amine function is protected, for example by t-butyloxycarbonyl.

Thus the first portion of the desired peptidic chain is obtained, which comprises two amino acids, and of which the terminal amine function is protected. As previously, the amine function is deprotected and it is then possible to proceed with the fixing of the third aminoacyl, under conditions similar to those of the addition of the second C-terminal amino acid.

Thus, one after the other, are fixed the amino acids, which will constitute the peptidic chain, to the amine group each time deprotected beforehand of the portion of the peptidic chain already formed, and which is attached to the resin.

When the whole of the desired peptidic chain is formed, the protective groups of the various amino acids constituting the peptidic chain are removed and the peptide is detached from the resin, for example, by means of hydrofluoric acid.

The invention also relates to the products obtained by conjugation (by covalent linking) between the peptides, such as defined above, and a macromolecular support of the type of those which can be used for the constitution of immunogenic active principles.

Such supports are well known to specialists. They can be natural supports, such as serum albumins, preferably human, when it relates to vaccines intended for man, or animal, when it relates to vaccines intended for veterinary use. Also will be mentioned by way of example of natural macromolecular supports, ovalbumins, tetanus toxin, etc. having molecular weights preferably higher than 20,000.

Recourse may also be had to synthetic macromolecular supports such as synthetic polypeptides. By way of example, are mentioned polylysines, bearing as the case may be side chains of polyalanine (the alanyl units being dextrogyratory and/or levogyratory). It is also possible to resort to synthetic chains, such as those described, for example, in French patent application No. 79 00819.

The active principles according to the invention are usable particularly for protecting subjects against papillomavirus, for example prior to the performing of an immunosuppressor treatment.

An important application resides in the production of further purified serums or antibodies, with a view to producing papillomavirus diagnosis reagents which can be used in routine tests, particularly at the time of vaginal smear examinations, or other gynecological examinations, for example in the case of detecting certain types of cancer of the uterine neck. They can also serve for preventive diagnosis tests in determatology.

The invention relates naturally also to all vaccine compositions, in which the abovesaid active principles are associated with pharmaceutical vehicles enabling their administration parenterally, orally or the like. These compositions contain possibly also an immunological adjuvant of the muramyl-peptide type, enabling reinforcement of the immunotory reaction with regard to the vaccinating principle.

These compositions can be used in human or veterinary medicine, the papillomavirus immunogenic sequences employed being then, as the case may be original, particularly as regards to those which include a high number of aminoacyl residues, of the papillomaviruses colonizing preferentially the tissues of the species for which the vaccine is intended.

Generally, the invention relates naturally to any DNA fragment of which the expression product in a suitable micro-organism contains at least one of the antigenic determinants of a human or animal papillomavirus, this fragment being characterized in that it comprises a nucleotide sequence, itself contained or similar to that contained either in the L1 region, or in the L2 region, or again for a part in the L1 region and for a part in the L2 region of that of the strands of the papillomavirus genome which includes them and which are capable of coding for structural proteins of the virus or for polypeptides having in common with these proteins a sequence containing at least one antigenic determinant characteristic of papillomaviruses.

It is understood that the claims which follow cover not only the corresponding DNA fragments and peptide fragments, but also all equivalents which can be produced, particularly but not exclusively in conformity with the indications which have been formulated in the present description.

The invention also relates to all DNA sequences extracted from the genome of papillomaviruses, other than those which have been mentioned above, particularly the sequences E1 (nucleotides 5473–6919) and E2 (nucleotides 6863–16) (in FIG. 2a at the level of the reading phases 1 and 2). The peptides expressed by these sequences can induce in vivo the formation of antibodies useful to detect lesions caused by papillomaviruses (and containing fragments of proteins and viral DNA) in conventional antibody antigen reactions detectable by conventional immunofluorescence or immunoenzymatic reactions, etc.

We claim:

1. A peptide sequence selected from the group consisting of

Leu-Asp-Gln-Phe-Pro-Leu-Gly-Arg-Lys-Phe-Leu,

Leu-Asp-Gln-Phe-Pro-Leu-Gly-Arg-Arg-Phe-Leu,

Ala-Lys-Arg-Arg-Arg-Lys, and

Ala-Lys-Lys-Lys-Lys-Lys.

2. The peptide of claim 1 which is

Leu-Asp-Gln-Phe-Pro-Leu-Gly-Arg-Lys-Phe-Leu.

3. The peptide of claim 1 which is

Leu-Asp-Gln-Phe-Pro-Leu-Gly-Arg-Arg-Phe-Leu.

4. The peptide of claim 1 which is

Ala-Lys-Arg-Arg-Arg-Lys.

5. The peptide of claim 1 which is

Ala-Lys-Lys-Lys-Lys-Lys.

* * * * *